(12) United States Patent
Chortyk

(10) Patent No.: US 6,605,598 B1
(45) Date of Patent: Aug. 12, 2003

(54) CHEMICALLY SYNTHESIZED SUGAR ESTERS FOR THE CONTROL OF SOFT-BODIED ARTHROPODS

(75) Inventor: Orestes T. Chortyk, Athens, GA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 1873 days.

(21) Appl. No.: 08/834,975

(22) Filed: Apr. 7, 1997

Related U.S. Application Data

(63) Continuation of application No. 08/323,403, filed on Oct. 14, 1994, now abandoned, which is a continuation-in-part of application No. 08/272,477, filed on Jul. 11, 1994.

(51) Int. Cl.[7] .................. A61K 31/715; C07H 17/00; C13K 5/00; A01N 25/00
(52) U.S. Cl. .................. 514/53; 536/4.1; 536/123.13; 536/124; 424/405; 424/DIG. 8
(58) Field of Search .................. 536/4.1, 123.13, 536/124; 514/53; 424/405, DIG. 8

(56) References Cited

U.S. PATENT DOCUMENTS

| | | | | |
|---|---|---|---|---|
| 4,148,924 A | * | 4/1979 | Smith et al. ............... | 514/725 |
| 4,337,080 A | * | 6/1982 | Szkrybalo ................. | 504/293 |
| 4,517,360 A | * | 5/1985 | Volpenhein ............... | 536/119 |
| 4,614,718 A | | 9/1986 | Seino et al. .............. | 435/72 |
| 4,683,299 A | | 7/1987 | Kea et al. ................. | 536/119 |
| 4,710,567 A | * | 12/1987 | Kea et al. ................. | 536/119 |
| 4,927,920 A | | 5/1990 | Wagner et al. ............ | 536/119 |
| 4,950,746 A | | 8/1990 | Navia ....................... | 536/119 |
| 4,980,463 A | | 12/1990 | Walkup et al. ............ | 536/124 |
| 4,983,731 A | * | 1/1991 | Wagner et al. ............ | 536/127 |
| 4,995,911 A | | 2/1991 | Matsumoto et al. ....... | 127/48 |
| 5,089,608 A | | 2/1992 | Walkup et al. ............ | 536/124 |
| 5,260,281 A | | 11/1993 | Pittarelli et al. ........... | 514/53 |

OTHER PUBLICATIONS

Chowdhary et al. *J. Chem. Soc Perkin Trans. I*, 1984, 419–427.*
Windholz et al., editors, "The Merck Index", Ninth Edition, Merck and Company, Rahway, New Jersey, 1976, monograph No. 8681, p. 1149.*
Severson et al. In *ACS Symposium Series*, "Bioregulators for Crop Protection and Pest Control", No. 557, Jun. 2, 1994, Chapter 9, pp. 109–121.*

Hough et al. *J. Chem Soc. Chem. Commun.* 1978, 664–665.*
Reinefeld et al. *Zucker*, 1968, 21(12), 330–338.*
Journal of Agricultural and Food chemistry, May–Jun. 1984, 566–570, by the American Chemical Society. Severson et al. Quantitation of the Major Cuticular Components from Green Leaf of Different Tobacco Types.
American Chemical Society, 1987, 220–238. Kabara, Jon J. Chapter 14, Fatty Acids and Esters as Antimicrobial/Insecticidal Agents.
Ent. Exp. & Appl. 5: 233–238, 1962. North–Holland Publishing Co., Amsterdam. Thurston et al. Toxicity of Nicotiana Gossei Domin to Myzus Persicae (Sulzer).
Journal of Economic Entomology 62(5):1115–1117, Oct. 1969. Burk et al. Resistance of Nicotiana Species to the Green Peach Aphid.
Journal of Economic Entomology 67(3):341–343. Received for publication Oct. 1973. Patterson et al. Twospotted Spider Mite Resistance in Nicotiana Species.
Entomol. Exp. Appl. 38:157–164, 1985. Jones et al. Wild Species of Nicotiana as a New Source of Tobacco Resistance to the Tobacco Hornworm Manduca Sexta.
Tob. Sci. 31:61–62, 1987. Neal et al. Nicotiana Species with High Resistance to Greenhouse Whitefly, Trialeurodes Vaporariorum.
American Chemical Society, 1994. Severson et al. Chapter 12, Aphicidal Activity of Cuticular Components from Nicotiana Tabacum.
Phytochemistry 32(4):859–864, 1993. Printed in Great Britian. Buta et al. Sucrose Esters from Nicotiana Gossei Active Against the Greenhouse Whitefly Trialeuroides Vaporariorum.
Journal of the American Oil Chemists Society 49:524–526, 1972. Weiss et al. Influence of Solvent on Degee of Acylation in the Formation of Sucrose Esters.
Journal of the American Oil Chemists Society 47:56–60, 1970. Feuge et al. Preparationof Sucrose Esters by Interesterification.
ACS Symposium Series 449. 1991. pp.264–277. Severson et al. Ovipositional Behavior of Tobacco Budworm and Tobacco Hornworm.
J. Amer. Soc. Hort. Sci. 115(1):161–165, 1990. Goffreda et al.

* cited by examiner

Primary Examiner—Kathleen K. Fonda
(74) Attorney, Agent, or Firm—John D. Fado; Gail E. Poulos

(57) ABSTRACT

The invention relates to an improved process for the synthesis and application of sugar esters, that are useful as effective, environmentally-safe pesticides for the control of soft-bodied arthropod pests.

15 Claims, 2 Drawing Sheets

CHEMICALLY SYNTHESIZED SUGAR ESTERS FOR THE CONTROL OF SOFT-BODIED ARTHROPODS

This application is a continuation of application Ser. No. 08/323,403 filed Oct. 14, 1994 abandoned, which is a continuation-in-part of application Ser. No. 08/272,477, filed Jul. 11, 1994, which is herein incorporated by reference in its entirety.

FIELD OF THE INVENTION

This invention relates to novel, synthesized, biologically active sugar esters, a method for making them, and to their use as effective, environmentally safe pesticides. In addition, a pesticide composition and a method of using the composition are disclosed. The novel compounds are capable of controlling arthropod plant pests such as greenhouse whiteflies, sweetpotato whiteflies, aphids and mites. The compounds can be applied as a dispersion in water.

BACKGROUND OF THE INVENTION

Arthropod plant pests cause extensive and severe damage to major agricultural commodities, both in the field and in the greenhouse environment. In addition to feeding damage, many of these insects also transmit viral diseases. Insects such as whiteflies and aphids deposit their excrement or "honeydew" on leaves, thus providing a favorable environment for the production of fungi such as sooty mold, which reduces photosynthetic activity and crop quality.

Infestations by the new B strain of the sweetpotato whitefly have proven particularly devastating to growers from Florida to California and as far north as New York and Ohio. The insect has a wide host range, which includes over 500 species of plants. Two dissimilar species, the greenhouse whitefly and sweetpotato whitefly, alone have caused economically significant damage to poinsettia, hibiscus, tomato, crossandra and other plants in a greenhouse environment. The greenhouse whitefly, native to North America, is now world wide in distribution and is resistant to most synthetic pesticides. The sweetpotato whitefly, not limited to the greenhouse environment, is particularly difficult to control on low crops, because it develops on the lower leaf surface that is difficult to adequately cover with pesticides. It also has the ability to change host plant and to acquire resistance to chemical pesticides. The recent rapid spread of strain B of this whitefly has caused significant economic losses to growers of cotton, melons, squash, sugar beets, lettuce, carrots, tomatoes, peanuts, alfalfa, and ornamental plants. In addition, it is a vector for more than 70 diseases including 25 viruses. Following serious whitefly infestations, several agricultural regions have been subjected to viral diseases such as pepper necrosis and yellowing of lettuce.

Whiteflies are generally tropical in distribution, however the sweetpotato whitefly is now believed to have spread in the United States with impunity because of a high level of insecticide resistance and insignificant natural enemies. There have been some efforts to establish populations of parasitoids, which apparently reduce or suppress the insect in its native habitat.

Currently, there are very few commercial pesticides that completely control whiteflies. The insect has a complex life cycle where the egg and pupal stages are generally resistant to chemicals. The entire life cycle is very short (approximately one month), resulting in a rapid increase in population. A severe infestation often occurs before a grower recognizes the problem, making eradication even more difficult. The infestations are rarely localized since the adult can readily take flight and the immature stages are distributed on bedding and ornamental plants. It can also develop a resistance to chemical insecticides fairly quickly, requiring control methods utilizing an alternative schedule of chemicals.

In choosing an effective pesticide, the mode of action is an important factor. The whitefly uses a piercing and sucking system to extract food from the phloem of the infested plant and its stylets can penetrate through a dry film of pesticide on plant tissue, without serious consequence from the pesticide. Therefore, control approaches are limited to either a systemic pesticide which penetrates the leaf surface or is absorbed by the roots and is ingested by the insect or a contact pesticide which penetrates or acts directly on the insect.

Long chain fatty acids (particularly $C_{12}$) and fatty acid soaps have been reported as effective in the control of insects (Kabara, ACS Symposium Series, No. 325, 1987). In addition, various species of Nicotiana plants have been shown to have resistance to infestation by green peach aphids (Thurston et al., Ent. Exp. & Appl., 1962 and Burk et al., J. of Econ. Ent., 1969), two-spotted spider mites (Patterson et al., J. of Econ. Ent., 1974), tobacco hornworm (Jones et al., Entomol. Exp. Appl. 1985) and greenhouse whitefly (Neal et al., Tob. Int., 1987). Recently, Goffreda et al., (J. Amer. Soc. Hort. Sci 115(1):161–165, 1990) indicated that epicuticular glucose esters were associated with aphid resistance in hybrids with wild tomato. Severson, et al., (Natural and Engineered Pest Management Agents, ACS Symposium series #551, 1994) showed that topical applications of sucrose esters to apterous aphids were toxic. Also, Buta et al., (Phytochemistry 32(4):859—864, 1993) have shown sucrose esters from Nicotiana gossei are potent pesticides against the greenhouse whitefly. As more and more studies are showing the potency of naturally-occurring sugar esters as pesticides, the need exists for the identification and development of specific synthetic sugar ester pesticides against soft-bodied arthropod insects. The advantage of sucrose esters is their superior control and their natural composition—fatty acids and sugar. Conventional pesticides are usually chlorinated or nitrated aromatics. The extraction of sucrose esters from plants of various species of Nicotiana is possible, although a labor intensive process. Various Nicotiana species have been grown and their cuticular sucrose esters extracted and characterized in a study of ovipositional behavior of the tobacco budworm (Severson, et al., Naturally Occurring Pest Bioregulators, ACS Symposium Series #449, 1991). It was found that sugar esters occurred in amounts of traces to 526 $\mu$g/cm$^2$ of leaf surface depending on the Nicotiana species. The most potent sugar esters came from plants such as Nicotiana gossei, which will yield at most about 120 mg/plant. Thus, natural plants will not likely become economical sources of millions of kilograms/year of sugar esters needed to control whiteflies or aphids in this country. Therefore, there is a need for a synthetic method for producing specific, biologically-active sugar esters which have the capacity of controlling whiteflies and other soft-bodied arthropod pests.

There are several methods for producing sugar esters on an industrial scale, as developed by the food industry in the early 1960's. High molecular weight fatty acid sugar esters, such as sucrose esters of palmitic, stearic, and oleic acids, are used in a wide variety of food products such as baked goods, beverages, spices, soups; in cosmetics such as soaps, lotions, creams; as emulsifying agents; bodying and bulking agents; and for encapsulating pharmaceuticals and other products. One method is a solvent process which produces sugar esters by reacting fatty acid methyl esters (FAME) with sucrose in solvents such as dimethylformamide or dimethylsulfoxide, in the presence of a basic transesterification catalyst and at a high temperature (Weiss, et al., J. Am. Oil Chem. Soc. 49:524, 1972). Sucrose polyesters can also be prepared by interesterification between molten sucrose and FAME of long chain fatty acids at 170°–187° C., catalyzed by lithium, sodium and potassium soaps in the absence of solvents (Feuge et al., J. Am. Oil Chem. Soc. 47:56, 1970). A less drastic process (e.g., U. S. Pat. No. 4,683,299) utilizes fatty acyl chlorides as acyl donors in anhydrous solvents. However, although the patent discloses that the reaction can be achieved at room temperature to 250° C., it is stated that the reaction should be initiated by adding the organic acid chloride slowly to the sugar-solvent mixture at relatively low temperatures of about 90° C. to about 116° C. At this temperature, the reaction is complete after 35 minutes. For temperatures from about 30° C. to 55° C., the time may range from 24 to 60 hours.

The principal objects of the present invention are to provide a novel method for synthesizing sugar esters of low molecular weight acids which does not require high reaction temperatures or an aqueous purification method and to demonstrate their biological activity.

SUMMARY OF THE INVENTION

It is therefore an object of the present invention to provide a method for synthesizing large quantities of sugar esters.

Another object of the present invention is to provide a method for synthesizing, at low temperatures, large quantities of low molecular weight aliphatic acid sugar esters.

A further object of the present invention is to provide a method for separating sugar esters into specific groups using anhydrous purification steps.

Another object of the invention is to provide novel, specific chemically synthesized sucrose esters having acyl substituents on both the fructose and glucose moieties.

A further object of the invention is to provide a pesticide composition comprising novel chemically synthesized sugar esters in a pesticidally effective amount.

A still further object of the present invention is to provide a method of treating soft-bodied arthropod plant pests by administering effective amounts of a pesticide composition containing sugar esters to areas suspected of infestation.

Further objects and advantages of the invention will become apparent from the following description.

DETAILED DESCRIPTION OF THE INVENTION

Figure 1A:
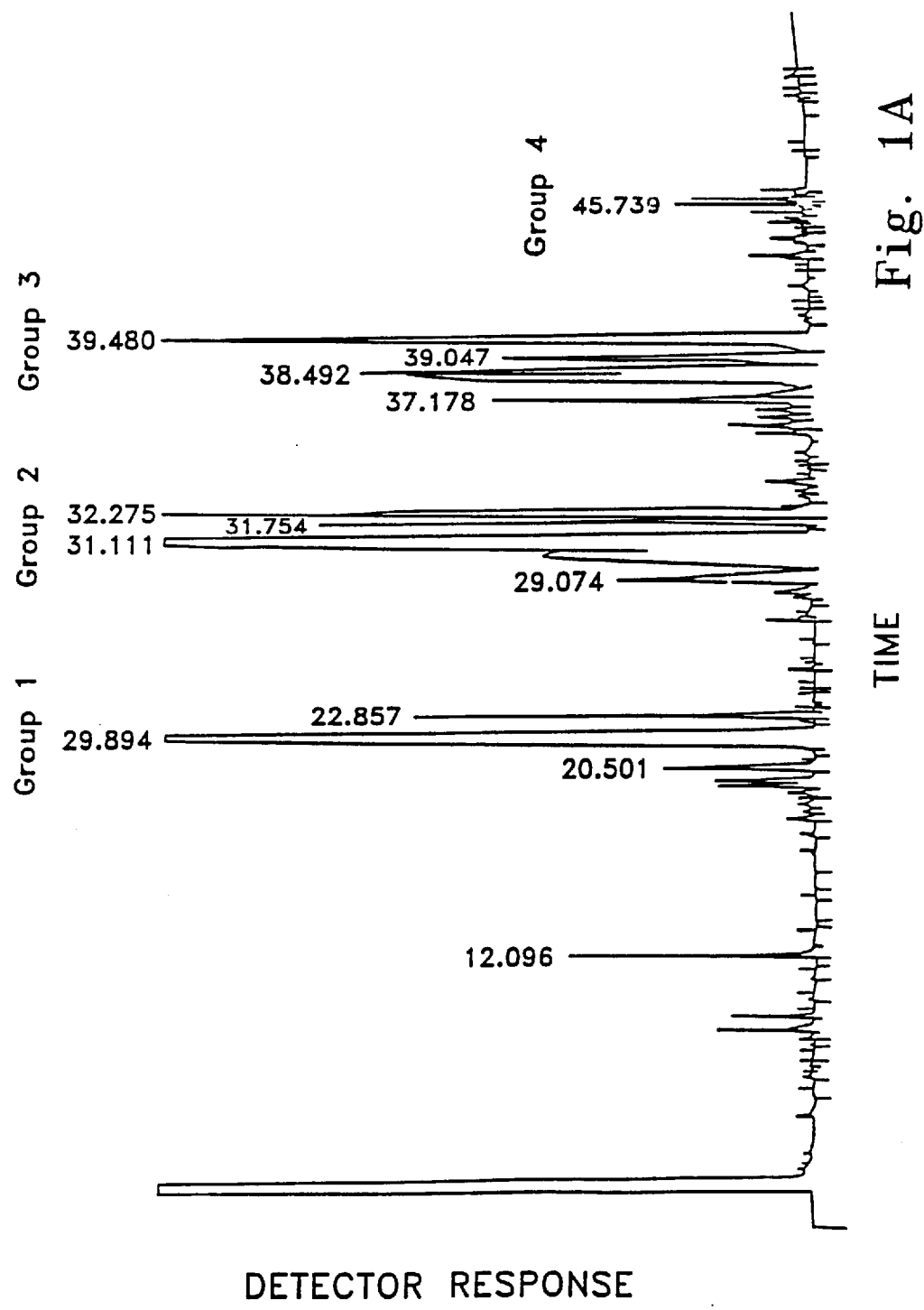
FIG. 1A is a gas chromatogram of the total preparation of sucrose ester groups from an octanoyl sucrose ester preparation.

The process of the present invention is particularly useful for the manufacture of specific sugar esters, designed especially for the control of soft-bodied arthropod pests such as aphids and whiteflies. This invention describes the preparation of lower molecular weight aliphatic acid sugar esters of defined biological activity against whiteflies and tobacco aphids. The described novel method for synthesizing specific sugar esters is important because it allows large quantities of the compounds to be produced in a relatively short period of time as compared to the labor intensive method of extracting sugar esters from leaves of green plants, as described in the Background of the Invention section of this Application.

The term sugar ester refers to a combination of carboxylic acids and a sugar molecule. The term sugar is meant to include any mono-, di-, or tri-saccharide and any of their reduced or oxidized forms that still possess hydroxyl groups. Non-limiting examples of saccharides include, for example, fructose, glucose, sucrose, rhamnose, galactose, lactose, arabinose, glucuronic acid, maltose, and raffinose.

Carboxylic acids, for the purpose of this application, include, for example., low molecular weight $C_4$ to $C_{12}$ aliphatic acids and their unsaturated, alkylated, substituted, oxidized, or hydroxylated derivatives such as, for example, butanoic acid, pentanoic acid, caproic acid, caprylic acid, 3-methylvaleric acid, 4-methylvaleric acid, hexanoic acid, 4-methylhexanoic acid, 5-methylhexanoic acid, heptanoic acid, 5-methylheptanoic acid, octanoic acid, nonanoic acid, capric acid, and lauric acid. Substituents on the aliphatic chain may include aryl groups, amino groups, formyl groups, ester groups, or other heteroatom groups.

As saccharides possess numerous free hydroxyl groups, the potential exists for the formulation of one or more ester linkages between one molecule of the saccharide and one or more carboxylic acids. Thus, for example, the esterification of sucrose with octanoic acid could result in the formation of the following 8 groups of sucrose esters (SE): monooctanoyl sucroses, dioctanoyl sucroses, trioctanoyl sucroses, tetraoctanoyl sucroses, etc. all the way up to octa-octanoyl sucroses.

The novel compounds produced by the method of the present invention have the following sucrose structures:

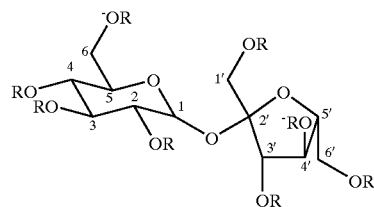

wherein R groups are either H (hydrogen) or acyl groups of straight chain or branched aliphatic acids, their unsaturated or hydroxylated derivatives, having four to twelve carbon atoms. The synthesized compounds possess either one acyl moiety and 7 free hydroxyls, two acyl moieties and 6 free hydroxyls, 3 acyl moieties and 5 free hydroxyls, 4 acyl moieties and 4 free hydroxyl groups, etc. up to 8 acyl substituents and no free hydroxyls. Sucrose esters containing only one acid belong to group 1 SE. As there are 8 hydroxyl groups in sucrose, esterifications yield 8 isomers of monoacyl sucrose. Group 2 SE, which have 2 acids esterified to 2 hydroxyls have a large number of isomers (27), due to the various combination of two positions. Similarly, group 3 SE have a large number of isomers, all of which have 3 acyl groups at various positions. The most potent pesticides have been determined to be the group 2 sucrose esters. Gas chromatography, mass-spectrometry, and nuclear magnetic resonance (NMR) spectroscopy have been used to characterize these SEs and to show that the most predominant Group 2 isomer has one acyl moiety on the glucose ring and one acyl moiety on the fructose ring.

Major Group 2 and Group 3 sucrose esters have the following structures:

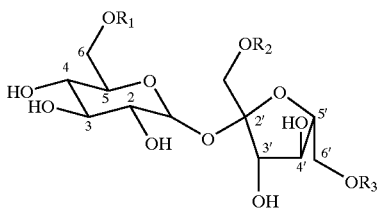

wherein $R_1$ and $R_3$ groups are straight chain or branched aliphatic acids, their unsaturated or hydroxylated derivatives, having four to twelve carbon atoms; and $R_2$ is either H (hydrogen) or straight chain or branched aliphatic acids, their unsaturated or hydroxylated derivatives, having four or twelve carbon atoms.

It has now been discovered that sugar esters which exhibit pesticidal activity against whiteflies and aphids can be synthesized at low temperatures of 60–65° C., by reacting sucrose, dissolved in dimethylformamide and pyridine, with acid chlorides dissolved in acetonitrile. This allows for kilogram quantities of sucrose esters to be prepared in relatively short periods of time (2 days for 1 lab technician) compared to the labor intensive extraction of sugar esters from the mixture of cuticular components of green leaves of specific plants.

Broadly, the process of the present invention comprises the step of reacting a sugar in an aprotic polar solvent with an aliphatic acid chloride in a solvent, at a temperature below the decomposition temperature of the sugar ester, to form the resulting sugar esters having a degree of substitution from 1 to 8. It is important that the acid chloride be added as a solution, otherwise degradations of products will be observed. Also, the other product of the reaction, hydrochloric acid, must be neutralized. It occurs as a complex with pyridine and this pyridine-hydrochloride is neutralized with sodium bicarbonate to prevent any possible degradation of the SE products by HCl. Next, the sugar esters solution is dried, filtered, and evaporated on a rotary evaporator to remove all solvents. The reaction product can then be dissolved in a suitable solvent and can be purified by column chromatography or can be used directly in a pesticide formulation.

Suitable organic solvents for dissolving the sugar are aprotic polar solvents such as, for example, dimethylformamide (DMF), dimethylsulfoxide (DMSO), or pyridine. For sucrose, the preferred solvent is DMF and sucrose readily dissolves, with heating, in a ratio of 1 g of sucrose per 2 ml of DMF.

Suitable organic solvents for adding the acid chloride to the sugar solution are slightly polar solvents which do not react with the acid chloride such as, for example, acetonitrile and acetone. Acid chlorides must be added as solutions in a suitable solvent, such as acetonitrile (1:1, W:V), as the direct addition of acid chlorides results in the partial degradation of the sugar esters (SE) product. An important criterion of the reaction is the molar ratio of sugar to acid chloride. It has been determined that the most active SE products result from the reaction of 1 mole of sugar with 2.5 moles of acid chloride. Higher molar ratios lead to the formation of increased quantities of group 4–8 sugar esters, containing 4, 5, 6, 7, or 8 acyl moieties per sugar molecule. Bioassay tests, described later, have indicated that group 2 sugar esters (having 2 specific acids per sugar molecule) are the most active pesticides. Thus, for example, for a 2.5:1 molar reaction ratio of octanoyl chloride to sucrose, the SE mixture in the reaction product is generally composed of about 25–35% monoacyl sucroses, about 35–45% diacyl-sucroses, about 10–25% triacyl-sucroses, and about 5–10% of tetra-acyl-sucrose esters, as determined by gas-chromatography (GC).

For column chromatographic separation into individual sugar ester groups, the total reaction product of sugar esters dissolved in chloroform is applied to a silica gel chromatography column prepared with methylene chloride. A solvent system of increasing percentages of methanol in methylene chloride is used to elute the various groups of sugar esters, that are collected in a series of fractions. The fractions are concentrated to dryness on a rotary evaporator, with a bath temperature of about 35° C. The residue is redissolved in a solvent such as acetone, acetonitrile, isopropanol or methanol for further GC analyses, acetone is preferred. Small aliquots are removed for characterization by gas chromatography, in order to determine which sugar ester groups are in each fraction.

The sucrose ester reaction products as well as the individual groups of sucrose esters may be used as a pesticide. Aqueous dispersions of sugar fractions are generally used in a concentration range of from approximately about 0.040% to approximately about 0.30%. A more preferred range is from approximately about 0.050% to approximately about 0.25%. The dried concentrated SE products are dissolved in acetone, methanol, or mixtures of methanol and acetone in a ratio of approximately about 1 methanol:10 acetone, volume to volume, and at most a ratio of approximately about 1 methanol:1 acetone, volume:volume, to form a solution having a concentration of from approximately about 1% to approximately about 10%, more preferably from approximately about 1% to approximately about 5%. The solution is added to stirred water to form a concentration of from approximately about 0.040% to approximately 0.30%, with a more preferred range of from approximately 0.050% to approximately about 0.25%. This forms a stable dispersion. The aqueous dispersions may be applied in high volume by a conventional sprayer at ambient temperature. It may be applied directly to the leaf surface.

The following examples illustrate the invention using the preparation of sucrose esters. They are intended to further illustrate the invention and are not intended to limit the scope as defined by the claims.

EXAMPLE 1

To maximize the formation of group 2 sucrose esters, 1 mole of sucrose is reacted with 2.5 moles of acid chloride. Sucrose is dissolved in dimethylformamide at a concentration of 54.8 grams (0.16 moles) of sucrose per 100 ml of DMF (in a 1 liter Erlenmeyer flask) with heating and stirring on a magnetic stirrer/hot plate, until the sucrose is dissolved. After complete dissolution of sucrose, approximately about 40 ml of pyridine are added and the solution is cooled to 60° C. The flask is returned to a magnetic stirrer plate, a thermometer is inserted into the flask, and the solution is stirred vigorously, as the acid chloride solution is added.

0.4 moles of acid chloride (such as butanoyl chloride, pentanoyl chloride, octanoyl chloride, heptanoyl chloride, nonanoyl chloride, decanoyl chloride, dodecanoyl chloride, etc.) is dissolved in approximately 100–150ml of acetonitrile, contained in a separatory funnel, and the solution is added at a fast drop rate to the sucrose solution, while stirring vigorously. The reaction temperature is maintained at approximately about 60–65° C., with cooling of the flask in a water bath as needed. The drop rate is adjusted so that it takes about 45 minutes to add the acid chloride solution. The reaction mixture is allowed to cool at room temperature and is then diluted with a double volume of acetone (acetonitrile or chloroform can also be used). About 40 grams of sodium bicarbonate and 20 ml of water are added for each 0.4 mole of acid chloride used in the reaction in order to decompose the pyridine hydrochloride by-product. Magnetic stirring produces the evolution of gaseous carbon dioxide from the reaction of the bicarbonate and hydrochloric acid. After about 15 minutes, the evolution of gas ceases and anhydrous, crystalline sodium sulfate is added to absorb the water. At this point, the reaction mixture should be clear and pale yellow or honey-colored. Any traces of brown color, caused by excessive heating or impure acid chlorides, can be removed by charcoal. The reaction mixture is then filtered through a medium porosity sintered glass funnel and evaporated to dryness on a rotary evaporator with the water bath temperature at approximately 45° C. A vacuum pump is required to evaporate off the dimethyl formamide. The SE product can be dissolved in a suitable solvent for subsequent insect bioassays (acetone) or for further chromatographic separations (chloroform).

EXAMPLE 2

Standard workup procedures for purifying sugar esters by heating the reaction product with aqueous solutions of sodium carbonate or bicarbonate and then extracting with ethyl acetate or chloroform are not applicable with the method of the present invention, as the low-molecular weight sugar esters (group 1 and group 2) may dissolve in water and would be lost.

Figure 1B:
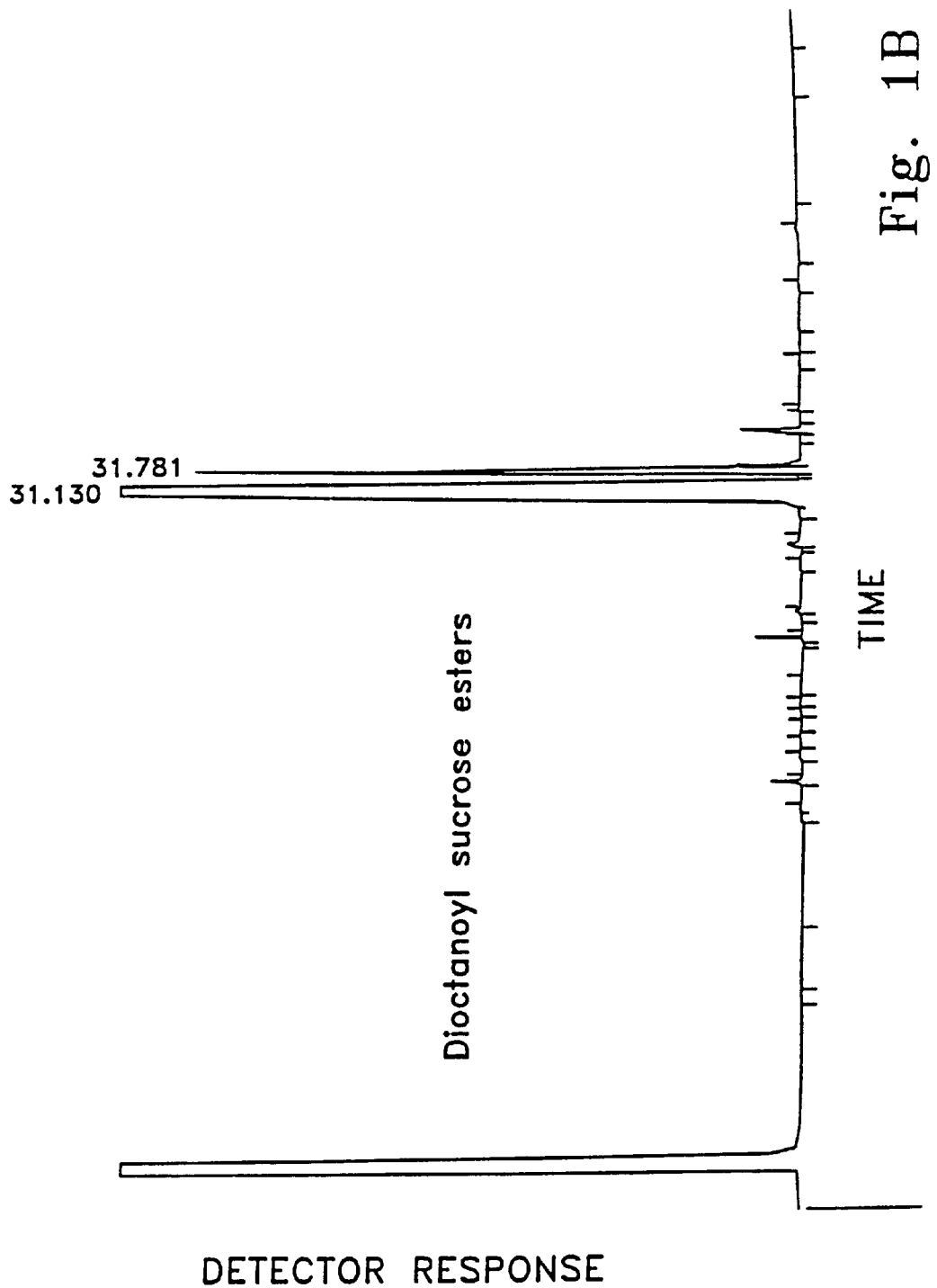
FIG. 1B is a gas chromatogram of the 7% methanol silicic acid column fraction containing only Group 2 octanoyl sucrose esters.

The reaction products, dissolved in chloroform, are separated on activated silicic acid (SA) using a solvent system of increasing percentages of methanol in methylene chloride. About 300 grams of 100–200 mesh silicic acid (Unisil SA from Clarkson Chemical Co. or 100 mesh Silicic Acid from Sigma Chemical Co.) is required to separate 15–20 grams of reaction product. The silicic acid, slurried in methylene chloride, is packed into a glass column (90×4 cm) equipped with a 500 ml reservoir and a ball joint at the top of the reservoir to allow the use of air pressure and clamps. The reaction product is added to the top of the SA column and air pressure at 2 psi is used to push the solvents more rapidly through the column. The column is eluted with 500 ml of 1% methanol in methylene chloride, followed by 500 ml each of 2%, 2.5%, 3%, 3.5%, 4%, 4%, 5%, 5%, 5.5%, 6%, 6%, 6.5%, 7%, 7%, 7.5%, 8%, 10%, 12%, 14%, and 16% methanol in methylene chloride. The small increases in the percentages of methanol are required to separate the individual groups of sucrose esters. The resulting chromatographic fractions are concentrated to dryness on a rotary evaporator at 35° C. in round bottom flasks. 5–6 ml of acetone are added to redissolve the residue and 2–3 μl are removed for gas chromatographic analysis. As an example, the SA separation of the octanoyl SE preparation yielded the fractions detailed in Table I below, with the distributions of the SE groups in each fraction having been determined from gas chromatograms. The success of the SA separation can be judged from gas chromatograms. The gas chromatogram of the total preparation is shown in FIG. 1A, while the gas chromatogram of the 7% methanol fraction, containing only Group 2 SE, is given in FIG. 1B. For bioassays, similar fractions are combined, evaporated to dryness on a rotary evaporator and then the sugar esters are redissolved in acetone for addition to a defined volume of water to produce the needed concentrations of insect spray solutions.

TABLE I

PERCENT DISTRIBUTION OF SUCROSE ESTER (SE) GROUPS IN CHROMATOGRAPHIC FRACTIONS FROM AN OCTANOYL SE PREPARATION

| Fraction[a] | SE Groups[b] | | | | |
|---|---|---|---|---|---|
| % CH$_3$OH in CH$_2$Cl$_2$ | 1 | 2 | 3 | 4 | 5 |
| 2 | | | 10 | 79 | 10 |
| 2.5 | | | 13 | 71 | 8 |
| 3 | | | 80 | 18 | |
| 3.5 | | 7 | 93 | | |
| 4 | | 35 | 64 | | |
| 4 | | 76 | 24 | | |
| 5 | | 90 | 8 | | |
| 5 | | 87 | | | |
| 5.5 | | 99 | | | |
| 6 | | 95 | | | |
| 6 | | 100 | | | |
| 6.5 | | 100 | | | |
| 7 | | 100 | | | |
| 7 | 6 | 94 | | | |
| 7.5 | 37 | 58 | | | |
| 8 | 80 | 20 | | | |
| 10 | 94 | 6 | | | |
| 12 | 99 | 1 | | | |
| 14 | 100 | | | | |
| 16 | 100 | | | | |

[a]Fractions from elution of 500 ml volumes of given solvent mixture.
[b]Calculated from peak areas of GC data for each fraction.

EXAMPLE 3

The sucrose esters obtained in the SA fractions as well as in the original reaction products are characterized by GC of their trimethylsilyl (TMS) ether derivatives. To form the volatile GC derivatives, sugar esters are derivatized by reacting them with N, O-bis-trimethyl silyl-trifluoroacetamide (BSTFA) and dimethylformamide (DMF) in GC autosampler vials, which are then sealed and heated at 75° C. for 1 hour (Severson et al., J. Agric. Food Chem. 32:566, 1984 which is herein incorporated by reference). One microliter samples are injected into a 0.32 mm×30 m glass capillary gas chromatographic column coated with a 0.1 μm of DB 5HT (J&W Scientific Co.). The GC oven is programmed from 200° C. to 400° C. at 3° C./min., the injection part of the instrument (Hewlett Packard 5890) was set at 350° C., the detector at 300° C., and the carrier gas (H$_2$) at 35 cm/sec.

Sugar esters result from the e4sterification of the free alcoholic hydroxyl groups by acids. Thus for the sucrose molecule, esterification by one molecule of acid will yield a monoester, by two acids a diester, etc. For esterification by one to eight acid groups, there will remain respectively, from seven to zero free hydroxyl groups which are amenable to TMS derivatization. In sucrose, acids can attach to the hydroxyls at the 6, 4, 3, or 2 carbon positions of glucose or at the 1', 3', 4' or 6' carbons of fructose. Thus, there are 8 possible monoesters, which compose the Group 1 sucrose esters, also called mono-acylsucroses. Similarly, Group 2 sucrose esters contain different di-acyl sucroses; with about 27 isomers possible for sucrose with two acyl groups at different positions. Evaluation of GC data for the total reaction product of an aliphatic acid chloride with sucrose in the 2.5:1 molar ratio indicates that Groups 1, 2, and 3 are predominantly formed and that each group contains one or two major isomers and numerous (4 or more) less abundantly occurring SE isomers. These points are illustrated in a typical gas chromatogram for an octanoyl SE preparation (see FIG. 1A).

In order to determine the structures of major Group 2 and Group 3 sucrose esters, the groups initially isolated from the SA column are separated by thin layer chromatography and LH-20 chromatography, followed by nuclear magnetic resonance spectroscopy (NMR) of the isolated compounds. Silicic acid chromatography fractions of the octanoyl SE preparation (described in Example 2) were selected for their high content of major Group 2 and Group 3 SE. These are subjected to a chromatotron (spinning thin-layer chromatography plate) separation to yield fractions enriched in the major isomers. The chromatotron fractions are then separated by subsequent LH-20 chromatography (using a chloroform-methanol solvent gradient) to yield the purified compounds. NMR analyses, which includes 22 proton NMR, carbon-13 NMR, broad-band decoupling and J-resolve experiment proves that the major isomer of Group 2 is 6,6'-dioctanoyl sucrose, shown below.

6,6'-di-octanoyl sucrose

This structural assignment confirms the GC/MS data that shows only mono-octanoyl glucose or fructose fragments, i.e. the original structure has 1 octanoyl group on each half of the sucrose molecule.

In a similar manner, NMR data shows that the major Group 3 sucrose ester is 6,1,6'-tri-octanoyl sucrose, shown below.

6,1',6'-tri-octanoyl sucrose

Again the GC/MS data confirms the structure. The MS fragments correspond to the monosaccharides with one or two octanoyl substituents, indicating 1 acyl group on one half and 2 acyl groups on the other half of the molecule.

As SE preparations for different aliphatic acids always produce identical GC chromatographic patterns for groups 2 and 3, it can be concluded that the major isomers produced in the described method are always the 6,6'-diacyl sucrose and 6,1,6'-triacyl sucrose compounds.

EXAMPLE 4

Bioassays of the total SE reaction products as well as of the individual groups of SE were conducted using the tobacco aphid, Myrzus Nicotiana Blackman, the greenhouse whitefly, Trialeurodes vaporariorum Westwood, and the sweetpotato whitefly, Bemisia tabaci Gennadius. Aqueous dispersions of sugar ester fractions, obtained from the column chromatographic step or the total reaction SE products were tested generally at a concentration of 1 mg/ml of water. To prepare the sprayable aqueous mixtures, a small amount of methanol (approximately about 20 $\mu$l per 10 mg of dried test compound) is added to the dried test compound. This is agitated gently. Then acetone is added to the methanol mixture to yield a concentration of approximately about 0.05 g/ml. This is shaken gently. To obtain a final, sprayable concentration of approximately about 1 mg sucrose ester/ml, about 10 ml of water are added to the mixture. This is then placed into an ultrasonic bath for 20 minutes. The resulting solution is ready to spray. Green-house reared apterous (wingless) aphids, that colonized a green tobacco plant, were removed with a leaf, sprayed, and kept in a closed petri dish. Percent mortality was determined after 24 hours. In a similar manner, bioassays against the green house whitefly or sweetpotato whitefly are conducted by spraying sucrose ester dispersions at 1 mg/ml of water onto whiteflies, trapped on a sticky surface, and determining percent mortality after 2–24 hours. Tables II and III below show the percent mortality of aphids treated by the individual sucrose ester groups and the total SE reaction products.

The results in Table II indicate that diheptanoyl- and dioctanoyl-sucrose esters produced the highest percent mortality when sprayed onto aphids. Sucrose esters of hexanoic acid (not shown) gave low percent mortality at about 23–43% mortality, while sucrose esters of higher fatty acids ($C_9$, $C_{10}$, $C_{12}$) produced progressively lower mortalities. In Table III, it is most interesting to see that the total reaction SE products derived from the heptanoyl and octanoyl sucrose esters were also highly active. Thus, heptanoyl and octanoyl SE preparations as well as their group 2 SE are potent pesticides against tobacco aphids.

Similar tests of group 2 sucrose esters against greenhouse whiteflies were conducted with group 2 SE isolated from total reaction products prepared at different times. See Table IV below. It can be seen that 100% whitefly mortality was achieved with sucrose esters for the composition range of diheptanoyl to didodecanoyl-sucrose esters. When total reaction SE products for the $C_7$ to $C_{12}$ SE were tested against the greenhouse whiteflies, similar dramatic results were obtained as shown in Table V below. It is thus apparent that the total SE reaction products, ranging from the $C_7$ to $C_{10}$ SE and containing Group 1 to Group 3 sucrose esters, are powerful whitefly pesticides. Thus, the total SE reaction products, while only containing about 40% of the Group 2 SE, are still potent pesticides.

As bioassay tests with the total SE mixtures against the greenhouse whitefly were successful, similar tests of the total SE reaction products were also conducted against the adult sweetpotato whitefly as shown in Table VI below. After only 2 hours, assay results indicate high biological activity for all of the total sucrose ester reaction products.

The one step reaction method described above produces total SE mixtures that are active against whiteflies. Thus, the synthetic method'yields large quantities of SE in a rapid manner and the simplicity of the developed procedure indicates that it should be readily adapted to commercial production.

TABLE II

BIOASSAY RESULTS OF DIFFERENT SUCROSE ESTERS (SE) AGAINST TOBACCO APHIDS

| SE[a] | No. of Tests | % Mortality[b] |
|---|---|---|
| monoheptanoyl sucrose | 1 | 17 |
| diheptanoyl sucrose | 3 | 88 |
| triheptanoyl sucrose | 2 | 16 |
| water | 3 | 5 |
| monooctanoyl sucrose | 1 | 11 |
| dioctanoyl sucrose | 3 | 88 |
| trioctanoyl sucrose | 2 | 27 |
| water | 3 | 5 |
| monononanoyl sucrose | 1 | 16 |
| dinonanoyl sucrose | 2 | 64 |
| tridnanoyl sucrose | 2 | 13 |
| water | 3 | 5 |
| monodecanoyl sucrose | 1 | 47 |
| didecanoyl sucrose | 3 | 43 |
| tridecanoyl sucrose | 2 | 15 |
| water | 3 | 5 |
| monododecanoyl sucrose | 1 | 47 |
| didodecanoyl sucrose | 2 | 23 |
| tridodecanoyl sucrose | 2 | 15 |
| water | 3 | 5 |

ND = Not Determined
[a]Tested at 1 mg SE/ml aqueous spray solution, average values for number of tests shown
[b]After 24 hours

TABLE III

BIOASSAY RESULTS OF THE TOTAL SUCROSE ESTERS (SE) REACTION PRODUCT AGAINST TOBACCO APHIDS

| Reaction Products[a] | % Mortality[b] |
|---|---|
| Total heptanoyl SE | 95 |
| Total octanoyl SE | 85 |
| Total nonanoyl SE | 75 |
| Total decanoyl SE | 64 |
| Control - water | 5 |

[a]Tested as an aqueous dispersion at 1 mg/ml (0.1%)
[b]After 24 hours

TABLE IV

BIOASSAY RESULTS OF DIFFERENT SUCROSE ESTERS (SE) AGAINST THE GREENHOUSE WHITEFLY

| SE[a] | No. of Tests | % Mortality[b] |
|---|---|---|
| dihexanoyl sucrose | 1 | 77 |
| diheptanoyl sucrose | 2 | 100 |
| dioctanoyl sucrose | 3 | 100 |
| dinonanoyl sucrose | 3 | 87 |
| didecanoyl sucrose | 2 | 100 |
| didodecanoyl sucrose | 1 | 100 |
| water | 3 | 5 |

[a]At 1.0 mg/ml spray solution, average value for number of tests shown
[b]After 24 hours

TABLE V

TEST RESULTS OF TOTAL SUCROSE ESTER REACTION PRODUCTS AGAINST THE GREENHOUSE WHITEFLY

| Reaction Products[a] | No. of Tests | % Mortality[b] |
|---|---|---|
| Total Hexanoyl SE | 1 | 64 |
| Total Heptanoyl SE | 1 | 100 |
| Total Octanoyl SE | 2 | 98 |
| Total Nonanoyl SE | 1 | 100 |
| Total Decanoyl SE | 2 | 92 |
| Total Dodecanoyl SE | 1 | 85 |
| Control - Water | 2 | 5 |

[a]Tested at 1 mg/ml aqueous spray solution
[b]After 24 hours

TABLE VI

TEST RESULTS OF TOTAL SUCROSE ESTER REACTION PRODUCTS AGAINST THE SWEETPOTATO WHITEFLY

| Reaction Products[a] | No. of Tests | % Mortality[b] |
|---|---|---|
| Total Hexanoyl SE | 3 | 80 |
| Total Heptanoyl SE | 3 | 95 |
| Total Octanoyl SE | 3 | 99 |
| Total Nonanoyl SE | 3 | 92 |
| Total Decanoyl SE | 3 | 80 |
| Control - Water | 3 | 5 |

[a]Tested at 1 mg/ml aqueous spray solution
[b]After 2 hours, only

The foregoing description is for the purpose of illustration. Such detail is solely for that purpose and those skilled in the art can make variations therein without departing from the spirit and scope of the invention.

What is claimed is:

1. A nonaqueous method for synthesizing low molecular weight aliphatic sugar esters comprising
   (a) dissolving a sugar in an aprotic polar organic solvent to form a first sugar solution,
   (b) dissolving an aliphatic acid chloride in a suitable solvent to form a first chloride solution,
   (C) adding pyridine to said first sugar solution to form a second sugar solution,
   (d) mixing said first chloride solution dropwise to said second sugar solution to cause an esterification reaction and form an esterification reaction solution,
   (e) adding a sodium bicarbonate solution after said esterification reaction to decompose any pyridine hydrochloride byproducts to form a product solution,
   (f) recovering sugar esters from said product solution to form a filtrate, evaporating said filtrate to dryness, and dissolving the dry filtrate in a solvent selected from the group consisting of acetone, methanol, chloroform, and mixtures thereof.

2. The method of claim 1, wherein the aliphatic acid chloride is the chloride of an acid selected from the group consisting of butanoic acid, pentanoic acid, caproic acid, caprylic acid, 3-methylvaleric acid, 4-methylvaleric acid, hexanoic acid, 4-methylhexanoic acid, 5-methylhexanoic acid, heptanoic acid, 5-methylheptanoic acid, octanoic acid, nonanoic acid, capric acid, decanoic acid, dodecanoic acid, and lauric acid.

3. The method of claim 1, wherein said aprotic polar organic solvent is selected from the group consisting of dimethylformamide, Dimethylsulfoxide, and pyridine.

4. The method of claim 1, wherein said suitable solvent for the aliphatic acid chloride is selected from the group consisting of acetonitrile and acetone.

5. The method of claim 1, wherein the molar ratio of sugar to acid chloride is 1:2.5.

6. The method of claim 1, wherein said esterification reaction is maintained at a temperature of approximately 60 to 65° C.

7. The method of claim 1, wherein said filtrate is dissolved in a solvent selected from the group consisting of acetone, methanol and mixtures thereof, to form a solution having a concentration of approximately about 1% to 10% weight/volume.

8. The method of claim 7, wherein said solution is stirred into water to form a sprayable aqueous solution having a concentration of approximately about 0.050% to 0.25% weight/volume.

9. The method of claim 1, wherein said filtrate is dissolved in chloroform to form a chloroform solution.

10. The method of claim 9, further comprising the steps of applying said chloroform solution to a chromatographic column, collecting fractions, drying said fractions and redissolving them in acetone, identifying the sugar ester in each fraction, and preparing a pesticide composition of each separate fraction by diluting the acetone solution with water to form a sprayable aqueous solution having a concentration of approximately 0.050% to 0.25%.

11. A pesticide composition effective for treating plants infested with arthiropod pests comprising an effective amount of a mixture of sugar esters produced by the method of claim 1.

12. A pesticide composition effective for treating plants infested with arthropod pests comprising an effective amount of a mixture of sugar esters produced by the method of claim 8.

13. A method for treating plants infested with arthropod pests comprising administering a pesticidally effective amount of the composition of claim 11 to pest infested plants.

14. A method for treating plants infested with arthropod pests comprising administering a pesticidally effective amount of the composition of claim 12 to pest infested plants.

15. A pesticide composition effective for treating plants infested with anthropod pests comprising a compound having the structure

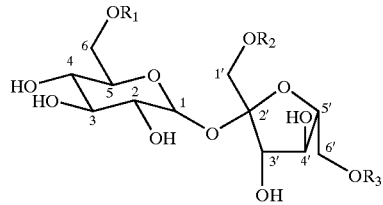

wherein $R_1$ and $R_3$ are —C—$R_4$ and $R_2$ is either H or —C—$R_4$ wherein $R_4$ is selected from the group consisting of $(CH_2)_2CH_3$, $(CH_2)_3CH_3$, $(CH_2)_4CH_3$, $(CH_2)_5CH_3$, $(CH_2)_6CH_3$, $(CH_2)_7CH_3$, $(CH_2)_8CH_3$, and $(CH_2)_9CH_3$, and and aqueous carrier.

* * * * *